United States Patent [19]
Vaillancourt

[11] Patent Number: 5,897,526
[45] Date of Patent: Apr. 27, 1999

[54] CLOSED SYSTEM MEDICATION ADMINISTERING SYSTEM

[76] Inventor: Vincent L. Vaillancourt, 14 Bunyan Dr., Livingston, N.J. 07039

[21] Appl. No.: 08/670,895

[22] Filed: Jun. 26, 1996

[51] Int. Cl.$^6$ .................................................. A61M 37/00
[52] U.S. Cl. ............................... 604/82; 604/85; 604/411
[58] Field of Search ............................... 604/82, 415, 86, 604/403, 408, 411

[56] References Cited

U.S. PATENT DOCUMENTS

| | | | |
|---|---|---|---|
| 4,573,967 | 3/1986 | Hargrove et al. | 604/411 X |
| 4,607,671 | 8/1986 | Aalto et al. | 604/415 X |
| 5,122,129 | 6/1992 | Olson et al. | 604/411 X |
| 5,649,907 | 7/1997 | Mori et al. | 604/82 X |

*Primary Examiner*—Wynn Wood Coggins
*Assistant Examiner*—N. Kent Gring
*Attorney, Agent, or Firm*—McAulay Nissen Goldberg Kiel & Hand, LLP

[57] ABSTRACT

The closed system medication administering system employs an adaptor having a hollow penetrating which can directly access a drug vial by piercing through a bung in the drug vial. A collapsible sleeve is placed around the hollow penetrating member and a membrane is disposed across the end of the sleeve to seal the hollow penetrating member when not in use. The hollow penetrating member also pierces the membrane when pushed into a drug vial. Resilient locking prongs may be provided to fixedly secure the drug vial to the adaptor or may be omitted. A reservoir bag may also be provided in a second line to fill with fluid from the primary line in order to effect reconstitution or dilution of a powdered or crystalline type drug in the drug vial. Simple manipulations of the unit consisting of the flexible bag, adaptor and drug vial allow the powdered drug to be reconstituted or diluted and subsequently dispensed.

25 Claims, 12 Drawing Sheets

CLOSED SYSTEM MEDICATION ADMINISTERING SYSTEM

This invention relates to a closed system medication administering system. More particularly, this invention relates to a system for the mixing of drugs in a sterile manner.

As is known, various types of drugs are packaged in glass or plastic vials normally called parenteral vials. Typically, these parenteral vials are intended to allow the drugs to have a long shelf life while being economically packaged. In addition, the known parenteral vials permit the drugs to be easily sterilized during packaging and to be subsequently accessed, for example by piercing a rubber bung with a needle or piercing pin.

Many of the known parenteral drug vials may be used as is. That is, a drug may be withdrawn from the vial using a syringe with a needle, piercing pin or blunt cannula attached. The syringe can then be used to inject the drug directly into an IV administration set.

As is also known, some parenteral vials contain a powdered drug or a crystalline drug solution which requires reconstitution. That is to say, a fluid, normally a saline solution, must be added to dissolve the drug and prepare the drug for further use. Still other parenteral vials contain drugs which must be further diluted before use.

Typically, a parenteral vial is formed of a glass or plastic bottle having a rubber bung secured in a mouth of the bottle and with a protective cap which closes over the bung in order to maintain the bung in place while also sealing the bung from the outside environment. In some cases, the bung may be pre-slit thereby enabling the use of a blunt cannula or other cannula penetrating devices.

A popular method in use for dispensing a drug from a parenteral vial is to remove the protective cap and to access the drug using a syringe with a needle or blunt cannula attached. After transferring the drug into the syringe, the drug is dispensed into an IV administration set normally after attaching a second needle or blunt cannula. Where the drug requires reconstitution, fluid is injected into the vial in order to dissolve the drug. Thereafter, the reconstituted drug may be withdrawn and injected into an IV administration set by the usual syringe needle/cannula combinations. While such procedures are, at best, attempts at an aseptic technique, these procedures involve multiple steps and are considered labor intensive.

Other types of systems have also been known, such as described in U.S. Pat. No. 4,434,822, to effect a sterile mixing of a drug in a vial for transfer into an IV administration set. Such a system employs a supplemental medication administering system to which the vial can be connected both for carrying out a diluting step and a subsequent dispensing step. However, this system requires the use of infrared radiation so as to effect a sterile connection between the vial and the supplemental medication administering system. Thus, this can be a cumbersome technique where a drug vial is to be quickly connected to an IV administration set in a simple efficient manner.

Other types of mixing devices have also been known, such as described in U.S. Pat. Nos. 4,458,733; 4,432,755; and 4,411,662. Such a mixing device employs a compressible chamber which includes a reservoir compartment and a gas trapping compartment which are segregated along the length of an internal wall. A means is also provided to access the gas trapping compartment by means of a needle disposed within a flexible sleeve having a membrane at one end to close the sleeve about the needle. Use is also made of a frangible cannula at an opposite end of the sleeve. When the vial is to be accessed, a mold is placed about a chamber access means and a container access means and molten material is injected into the mold not only to sterilize the end portions of both access means but also to form a unitary molded junction which encloses the end portions of the two components. Obviously, one of the disadvantages of such a system is the need to employ molten material which is hot and which is cumbersome to use.

Accordingly, it is an object of this invention to provide a simple technique for connecting a drug vial to an IV administration set.

It is another object of the invention to use relatively simple mechanical techniques for securing a drug vial to an IV administration set.

It is another object of the invention to be able to dispense drugs from parenteral vials directly into an IV administration set without the need for syringes and needles.

It is another object of the invention to permit parenteral vials to be attached multiple times without compromising sterile procedure techniques.

It is another object of the invention to connect different types of parenteral vials to an IV administration set without compromising sterile procedure techniques.

It is another object of the invention to be able to reconstitute a drug or to further dilute a drug prior to being dispensed from an IV administration set.

Briefly, the invention is directed to a closed system medication administration system which includes an IV container, such as a bag, for dispensing a fluid under gravity, a primary line communicating with the IV container to receive and convey fluid therefrom and an access device communicating with the primary line to deliver fluid to a patient.

The invention provides such a system with an adaptor for coupling with a drug vial and which includes a collapsible sleeve with a membrane disposed across one end to seal against the drug vial and a hollow penetrating member contained within the sleeve for penetrating through the membrane into the vial in response to collapsing of the sleeve. The system also uses a second line to communicate with the penetrating member to receive the contents of the drug vial and communicates with the primary line to deliver the vial contents thereto.

When in use, a drug vial formed of a bottle, a rubber bung in a mouth of the bottle and a protective cap is coupled to the adaptor. In this respect, the vial is pressed or abutted against the adaptor so that the collapsible sleeve collapses thereby allowing the penetrating member to pierce through the membrane of the sleeve and to pass through the rubber bung into the bottle. Prior to this step, the exposed surfaces of the membrane and the rubber bung may be wiped with a suitable disinfectant agent. Once the penetrating member has pierced through the rubber bung, the friction force between the bung and the member should be sufficient to retain the member in place in a secure coupled manner. Alternatively, in order to ensure a locked coupling arrangement, the adaptor may include a resilient locking means for releasably engaging with the drug vial.

The adaptor may also include an air vent for venting air therefrom and a cap for selectively sealing the air vent. Such an air vent may be in the form of a vented filter.

In one embodiment, the second line may be primed prior to the vial attachment. To this end, a releasable clamp is provided on the second line for selectively blocking flow through the second line. When the clamp is opened, fluid may flow from the primary line into the second line up to the adaptor. Of course, during this time, the air vent is uncapped so as to permit air to exhaust from the second line. After the second line has been primed, both the vial bung and vial adaptor are wiped with a suitable antiseptic, such as Betadine-povidone iodine. The vial is then attached to the adaptor. Next, the vial adaptor is raised above the level of the fluid in the primary line so that fluid may now flow from the drug vial through the second line into the primary line. In order to prevent any back flow of the fluid from the second line up into the primary line towards the IV bag, a back check valve or a clamp may be provided in the primary line to prevent such a retrograde flow.

Once the fluid in the second line reaches the level of the fluid in the primary line, the flow in the primary line is re-instituted and takes over from the second line.

Once the drug vial has been emptied, the vial may be left in place or removed. In either case, the action of the primary line will not change. Should the second line be lowered below the fluid height of the primary line, then either the clamp on the second line should be closed or alternately, the air vent capped. This will effectively seal the line off from fluid movement back into the second line.

When another vial is to be used, the first vial is removed below the fluid height of the primary line. The clamp in the second line is then opened to prime the second line. Alternatively, the cap of the vent filter may be removed. After priming, both the bung of the drug vial and the membrane of the collapsible sleeve are wiped with an antiseptic prior to connection. In this manner, a sterile connect procedure is utilized.

When a drug vial is to be reconstituted, the second line is first primed in the above manner. After priming, the drug vial is attached and while keeping the vial below the fluid level of the primary line, the vial is allowed to fill with fluid from the second line. Care must be exercised to ensure that fluid does not enter the air vent portion of the penetrating member and shut down the filling of the vial. Should this occur, the nurse or other technician may eliminate the fluid in the vent by raising the level of the vial sufficiently, for example just to above the level of the primary line fluid to initiate venting but not sufficient for fluid flow. After filling the vial, the second line is clamped off and the vial shaken to complete the reconstitution process. The clamp is then opened or the vent cap removed. In this respect, the vent must be open to atmosphere to effect a flow. The vial is then raised above the level of the primary line fluid level. The drug will now flow from the vial into the primary line.

When a drug is to be diluted prior to delivery into the primary line, a flexible or semi-flexible bag is disposed between and in communication with the penetrating member and the second line to receive fluid from one end of the penetrating member. In particular, the flexible bag functions as a fluid reservoir. Initially, this reservoir is one-half to three-quarters filled with fluid from the primary line. After the vial is attached, the primary line is clamped off to initiate flow. Alternatively, the vial may be raised above the level of the primary line fluid to initiate flow. The contents of the vial will now empty into the reservoir. A small amount of external agitation should be sufficient to dilute the drug in the reservoir. With the vent opened, the diluted drug will now flow into the primary line.

The flexible bag which acts as a reservoir may also be mounted on a support on one exterior side of the bag while a pull tab is secured to the opposite exterior side of the bag. Such a tab is used to selectively pull the sides of the bag apart in order to draw a vacuum in the spike for emptying the contents of a drug vial. Alternatively, a pull tab may be secured to an end face (side) of the bag for pulling apart of the bag and this support eliminated.

In another embodiment, the closed system medication administering system employs an IV container for dispensing a fluid under gravity, a volumetric set, e.g. a Buretrol volume control tube connected to the IV container to receive fluid therefrom, a drip chamber extending from the tube and a primary line extending from the drip chamber to convey fluid therethrough. In accordance with the invention, an adaptor is provided on one end of the tube for coupling with a drug delivery means such as a drug vial. In addition, the adaptor includes a collapsible sleeve, as above, with a membrane disposed across one end to seal against the drug delivery means and a hollow penetrating member concentrically within the sleeve for piercing through the membrane into the drug delivery means in response to the sleeve collapsing. In addition, an air vent is also provided on the end of the tube for venting air therefrom.

Still further, an air vent may be provided on the adaptor to vent air. In this embodiment, in order to dilute a drug, the tube is filled to a desired level and the primary line is shut down. The drug vial may then be connected via the adaptor and emptied into the tube for dilution and dispensing.

In still another embodiment, a bag for receiving fluid may be provided with a line extending from the bag to convey fluid and an adaptor for coupling with a drug vial. As above, the adaptor includes a collapsible sleeve with a membrane and a penetrating member with the penetrating member being in communication with the bag.

In this embodiment, the line which extends from the bag may be attached to a Y-Site or injection port. The bag may be pre-filled or partially filled with an IV fluid. The vial is attached to this closed system in a sterile connect manner as above and the drug is either reconstituted or transferred directly into the bag. Afterwards, the line leading from the bag is primed in the usual way and then connected to an injection port, in which case, an attached flow control clamp controls the flow to the injection site to a Y-Site of a primary line, in which case, the bag is elevated above the level of fluid in the primary line and flow then controlled in the usual manner.

The penetrating member which is used in the above embodiments may have one or two lumens. One lumen is provided for fluid flow and the second lumen is provided for air passage. The end of the air passage lumen also contains a filter and may also have a cap for the filter.

The membrane on the collapsible sleeve may be of rubber, silicone, elastomer or other penetrable material which has closure properties. Should the penetrating member need only be used once, then any membrane material which can be opened one time without regard for closure may be used. The penetrating member may be metal or plastic with a tip preferably having a piercing point. However, if a slit septum membrane is used, and the penetrating member is to interface with needleless access bungs, the penetrating member may have a blunt, rounded or most any other type of configuration at the tip.

In most cases, a second lumen on or near the penetrating member is required to vent air into the vial as fluid is being withdrawn. Generally, the air vent lumen is positioned higher than the fluid removal lumen. Such an air vent lumen will terminate in a filter generally of the microbial barrier type to prevent contamination from entering the system and fluid from leaving the system.

In another embodiment, an injection port with or without a pre-slit septum is attached to a flexible bag or tubing of an IV Administration Set. A syringe or other external fluid reservoir has an outlet connection which is a penetrating member. In addition, a rubber collapsible sleeve is mounted over the penetrating member. When force is applied to the penetrating member, the member penetrates the injection port thereby effecting fluid communication by first penetrating the face of the collapsible sleeve and the injection port rubber member. A disinfectant (sterilizing agent) is wiped over the surfaces of the face of the sleeve member and the rubber member of the injection port prior to attachment. In this manner, a sterile connection is achieved.

These and other objects and advantages of the invention will become more apparent from the following detailed description taken in conjunction with the accompanying drawings wherein:

Figure 1:
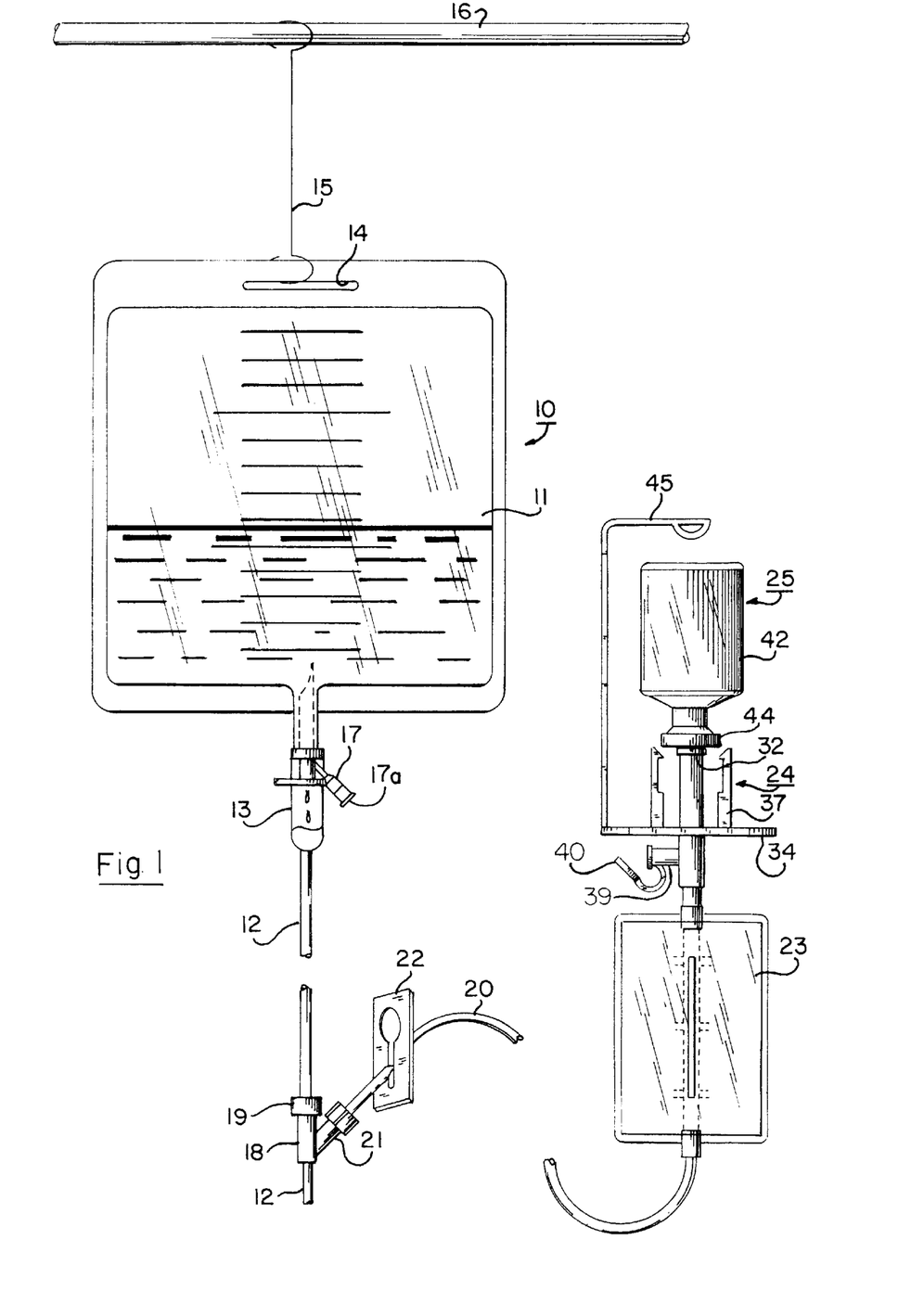
FIG. 1 illustrates a closed system medication administering system constructed in accordance with the invention.

Referring to FIG. 1, the closed system medication administering system includes an IV container such as a plastic bag for dispensing fluid 11 under gravity and a primary line 12 communicating with the IV bag 10 via a drip chamber 13 in order to receive and convey fluid therefrom. As indicated, the IV bag 10 has a slot 14 which allows the bag 10 to be suspended by a hanger 15 from a suitable support, such as an IV pole (not shown). In addition, an air vent 17 with a filter 17a is in communication with the bag 10 upstream of the drip chamber 13 for conventional purposes, i.e. to allow the bag 10 to drain.

As shown, a Y-Site connector 18 is disposed within the primary line 12 with a back check valve 19 in the primary line 12 to prevent back flow of fluid.

A suitable access device (not shown) and flow control device (not shown) communicate with the distal end of the primary line 12 to deliver fluid to a patient.

In addition, a second line 20 extends from one arm 21 of the Y-Site connector 18 and has a releasable clamp 22 thereon for selectively blocking flow through the second line 20.

The second line 20 extends to a flexible bag 23 which functions as a fluid reservoir. This bag 23 is, in turn, connected to an adaptor 24 for coupling with a parenteral drug vial 25.

Figures 6, 7:
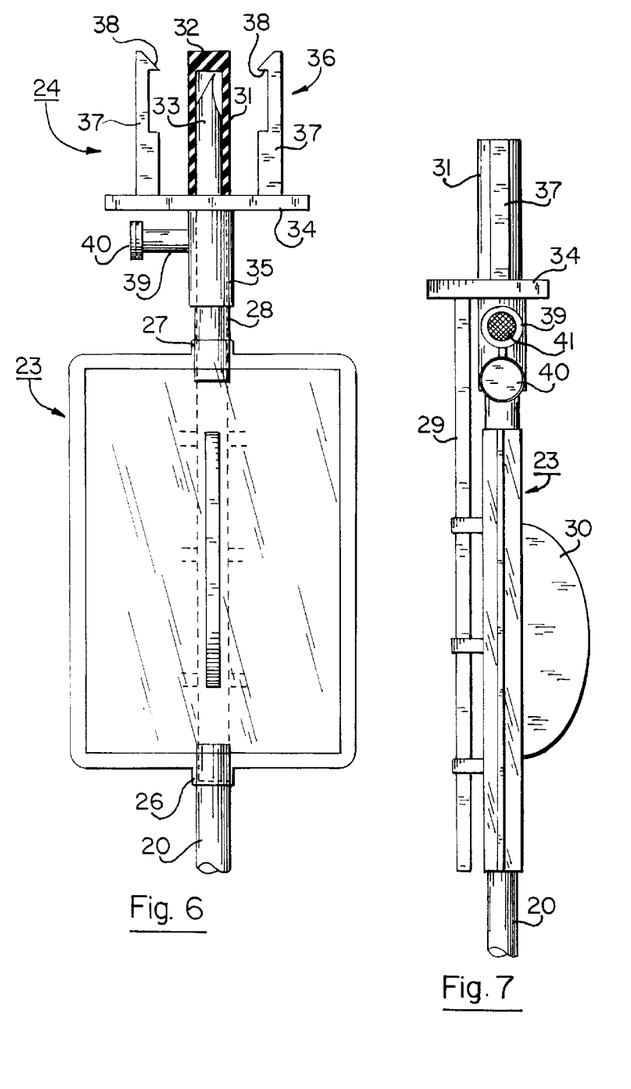
FIG. 6 illustrates a side view of a reservoir bag incorporated into the medication administering system in accordance with the invention.
FIG. 7 illustrates a side view of the reservoir bag and mounting arrangement in accordance with the invention.
Figure 8:
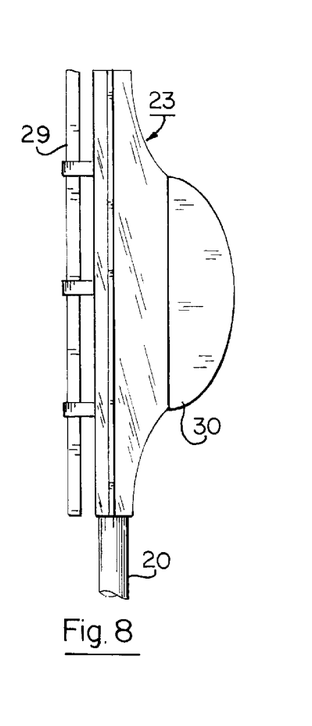
FIG. 8 illustrates a partial view of the reservoir bag in an outwardly extended position.

Referring to FIGS. 6, 7 and 8 wherein like reference characters indicate like parts as above, the flexible bag 23 is formed of two sheets which are sealed together at the periphery. The bag 23 has a port 26 communicating with the second line 20 and a port 27 which communicates with a port 28 of the adaptor 24. As indicated in FIG. 7, a support 29 which descends from the adaptor 24 is secured to one side of the bag 23 while a pull tab 30 is secured to the opposite side of the bag. The pull tab 30 may be pulled manually so as to pull the two sides of the bag 23 apart thereby drawing a vacuum in both the line 20 and the adaptor 24 for purposes as described below. FIG. 8 illustrates the bag in the pulled-out condition.

There may be situations in which for one reason or another, the drug will not drain from the drug vial 25 even when the vent 39 is opened. In such situations, pulling of the flexible bag 23 apart creates a slight negative pressure in the bag which immediately causes the reconstituted drug to empty from the drug vial into the bag.

The flexible bag 23 also eliminates any tendency for air to pass down the second line 20 and to enter into the primary line 12 of the IV administration. In this respect, the bag 23 behaves very much like an air trap eliminating the need for any air venting filter in the line.

Referring to FIG. 6, the adaptor 24 includes a collapsible sleeve 31 with a membrane 32 disposed across one end to seal against the drug vial 25 (see FIG. 1) as well as a hollow penetrating member 33 which is disposed concentrically within the sleeve 31 for penetrating through the membrane 32 into the drug vial 25 in response to collapsing of the sleeve 31.

As shown in FIG. 6, the adaptor 24 includes a base plate 34 from which the sleeve 31 extends and to which the sleeve 31 is secured in a sealed manner. The base plate 34 is integrally formed or connected with a spigot 35 which extends downwardly, as viewed, and from which the port 28 extends. As indicated, the hollow penetrating member 33 extends through and is connected in the spigot 35 and communicates with the bag 23 so as to convey fluid therebetween.

As indicated in FIG. 6, a resilient locking means 36 forms part of the adaptor 24 for releasably engaging with a drug vial 25. As indicated, this locking means 36 may be formed of at least one pair of oppositely facing prongs 37, each of which has at least one inwardly directed projection 38 for engaging with a recessed portion of a drug vial 25. As indicated, each prong 37 extends upwardly from the base plate 34.

As also shown in FIGS. 1 and 6, an air vent 39 connects to the spigot 35 of the adaptor 24 for venting air therefrom while a removable cap 40 is provided for selectively sealing the air vent 39. As indicated in FIG. 7, the air vent 39 has a filter 41 mounted at the end which is of conventional structure.

Referring to FIG. 1, the drug vial 25 is of a conventional type having a plastic or glass bottle 42 in which a rubber bung 44 is mounted and is normally protected by a plastic flip top protective cap (not shown) which has been previously removed.

As also shown in FIG. 1, a hanger 45 of skeletal shape is secured to the base plate 34 of the adaptor 24 in order to permit suspension of the vial 25 and adaptor 24 from a suitable support (not shown).

In use, the drug vial 25 is simply pressed against the membrane 32 while becoming locked in place within the prongs 37 of the adaptor 24. In this respect, the projections 38 of the prongs 37 engage the recess (neck of the vial 25) between the flanged opening and the vial which contains the parenteral fluids.

Figure 2:
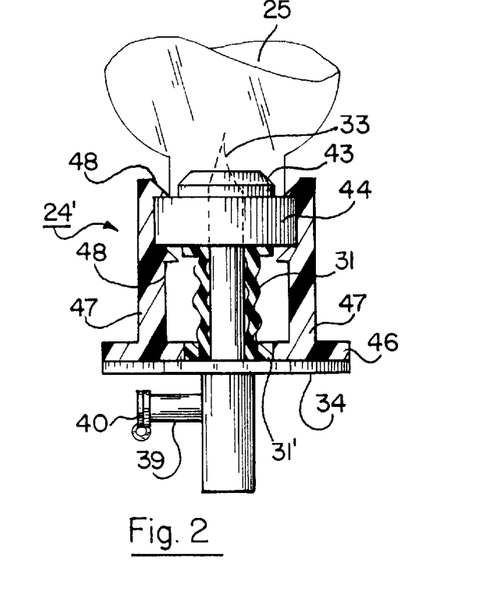
FIG. 2 illustrates a part cross-sectional view of an adaptor constructed in accordance with the invention.
Figure 3:
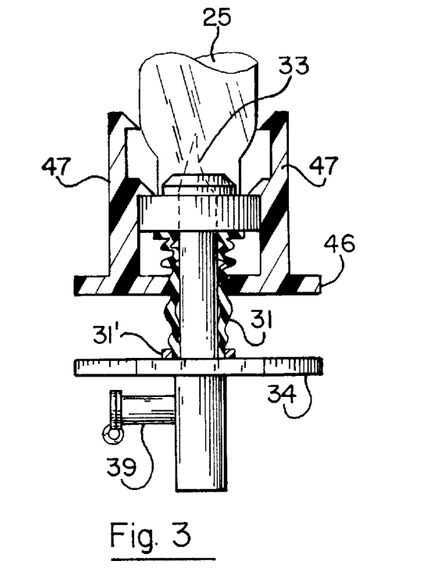
FIG. 3 illustrates a view similar to FIG. 2 of the adaptor in a locking position on a drug vial in accordance with the invention.

Referring to FIGS. 2 and 3 wherein like reference characters indicate like parts as above, the adaptor 24' may have a movable locking means for coupling with the drug vial 25. In addition, the adaptor 24' is constructed so as to accept two sizes of parenteral vials, such as a 20 millimeter size (FIG. 2) or an 11 millimeter size (FIG. 3). As indicated in FIG. 2, the larger vial is secured with the prongs 48 locking the vial in place. In operation, the vial is pushed down over the adaptor 24' to cause the penetrating member 33, for example in the form of a spike, to pierce the membrane of the collapsing sleeve 31 as well as the rubber bung 44 thereby establishing flow of communication in a closed system manner.

Referring to FIG. 3, the adaptor 24 is able to hold the smaller vial 25 in the lower securement section. After attachment of this vial to the adaptor 24, the base plate 34 of the adaptor 24' is pushed upward with first the face of the membrane of the sleeve 31 engaging the upper bung 44. As the sleeve 31 collapses, the penetrating member, i.e. a spike 33 pierces the membrane of the sleeve 31 and the bung 44. When the desired depth of penetration of the spike 33 is obtained, further pressure on the base plate 34 is removed. The spike 33 is now in the vial at the desired depth, for example as illustrated in FIG. 3. The frictional resistance between the spike 33 and the rubber bung 44 is normally sufficient to prevent the spike 33 from further movement. If desired, a yoke (not shown) may be connected between the base 46 and base plate 34 of the adaptor.

As indicated, the locking means is formed with a base plate 34, as above, and a separate movable annular part 46. As indicated, the annular part 46 is in the form of a disc for seating on the base plate 34. In addition, this annular disc 46 has prongs 47 which extend upwardly with each prong 47 having a pair of projections 48 thereon.

As shown in FIG. 2, the collapsible sleeve 31 is concentrically disposed within the annular part 46. Further, as shown in FIG. 3, the annular part 46 is movable relative to the base plate 34. At the same time, the collapsible sleeve 31 is anchored to the base plate 34 and about the spike 33 via an annular ring 31'.

Figure 4:
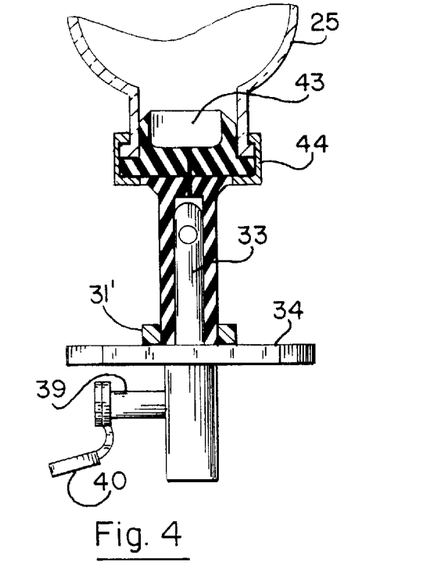
FIG. 4 illustrates a modified adaptor without a releasable locking means.
Figure 5:
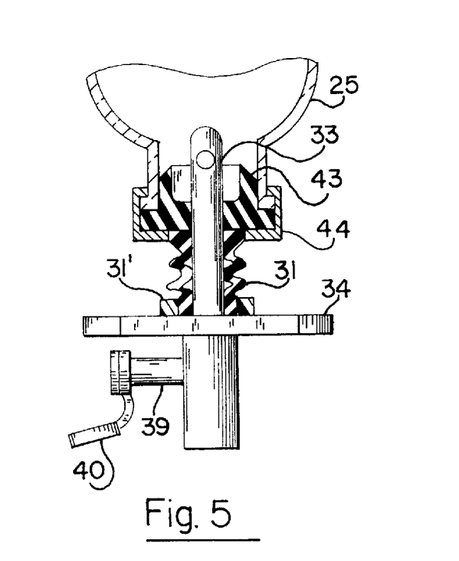
FIG. 5 illustrates a part cross-sectional view of the adaptor of FIG. 4 with a hollow penetrating member penetrating through the bung of a drug vial.

Referring to FIGS. 4 and 5, wherein like reference characters indicate like parts as above, the adaptor 24 may be constructed without the resilient locking means. In this case, once the hollow penetrating member 33 (for example, a blunt cannula for use with a pre-slit membrane and pre-slit bung 43) has penetrated through the pre-slit bung 43 as indicated in FIG. 5, the friction forces between the bung 43 and the penetrating member 33 should be sufficient to hold the vial 25 coupled to the adaptor 24.

Referring to FIG. 6 wherein like reference characters indicate like parts as above, in order to connect a drug vial to the adaptor 24, the exposed surfaces of the membrane 32 and the rubber bung 43 (see FIG. 1) are wiped with a suitable disinfectant. Next, with the adaptor 24 being positioned below the level of fluid in the IV bag 10 (FIG. 1), the drug vial 25 is snapped into place between the prongs 37 of the adaptor 24. At this time, the spike 33 pierces through the membrane 32 while also piercing through the bung 43 of the drug vial 25.

The flexible bag 23 or a semi-rigid bag (not shown) as typically used in small volume containers for the addition of drugs in IV therapy is primed to have fluid from the IV bag 10 delivered thereto. To this end, the clamp 22 is released and the flexible bag 23 placed below the level of fluid in the IV bag 10. Fluid is thus allowed to pass from the primary line 12 through the arm 21 of the Y-Site connector 18 into the second line 20 and thus, into the bag 23. After the appropriate amount of fluid has been obtained in the bag 23, the clamp 20 is again clamped onto the second line 20 to prevent further flow through the second line 20.

Figure 9:
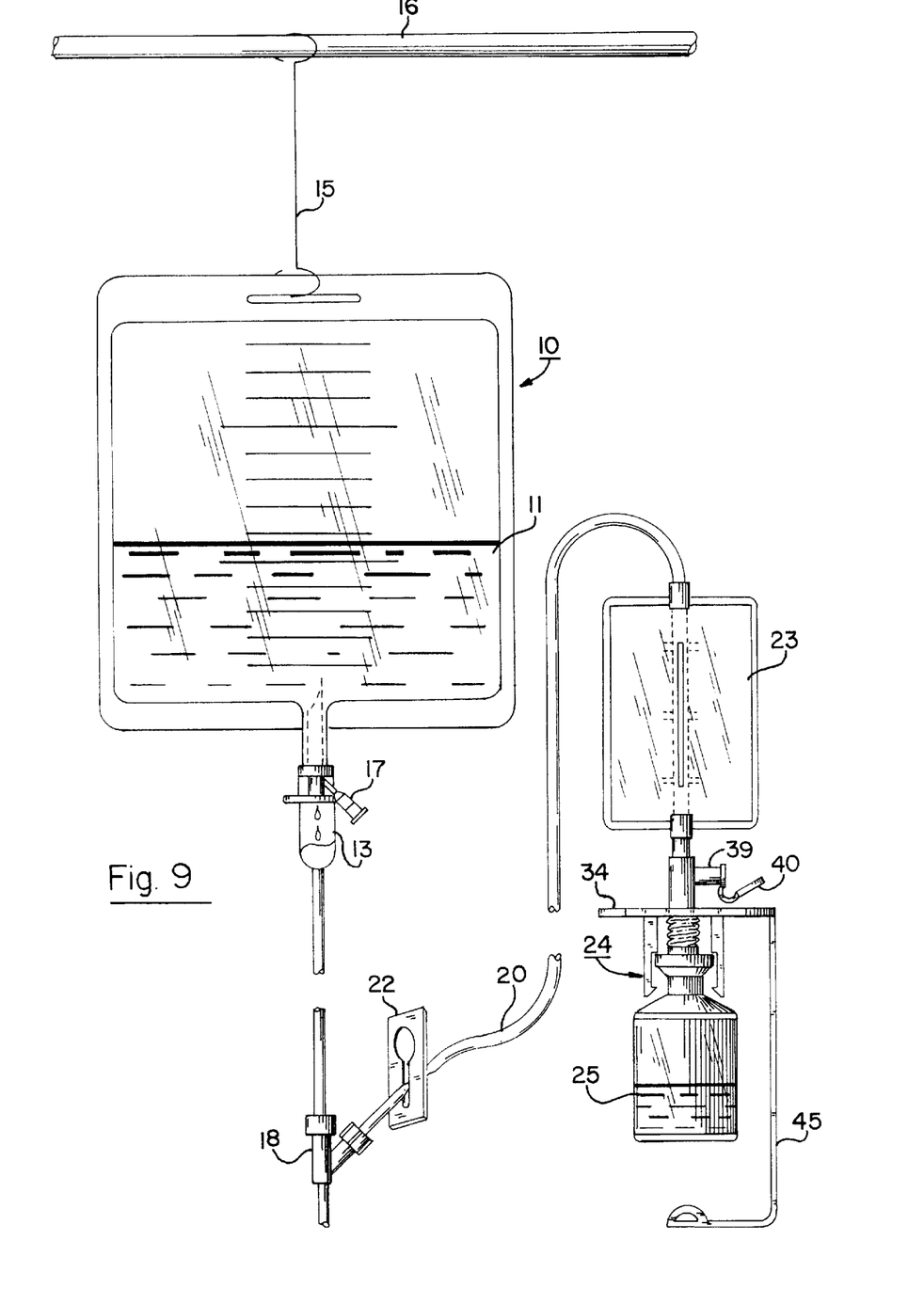
FIG. 9 illustrates a view of the medication administering system during a drug dilution step.

After the penetrating member 33 is penetrated into the drug vial 25, the unit consisting of the flexible bag 23, adaptor 24 and drug vial 25 is turned upside down to the position indicated in FIG. 9. This will permit fluid from the flexible bag 23 to pass through the penetrating member into the drug vial 25 to dilute the powdered drug. During this procedure, the air vent 39 vents air to the atmosphere via the filter 41 as the drug vial 25 is filling.

After a suitable amount of fluid has been passed into the drug vial 25, the vial may be agitated. Thereafter, the unit consisting of the flexible bag 23, adaptor 24 and vial 25 is returned to the position as shown in FIG. 1 so as to be suspended above the level of fluid in the IV bag 10.

There may be situations in which for one reason or another, the drug will not drain from the drug vial 25 even though the vent 39 is opened. In such situations, pulling of the flexible bag 23 apart creates a slight negative pressure in the bag which immediately causes the reconstituted drug to empty from the drug vial into the bag.

The flexible bag 23 also eliminates any tendency for air to pass down the second line 20 and to enter into the primary line 12 of the IV administration set. In this respect, the bag behaves very much like an air trap eliminating the need for any air venting filter in the line.

When the contents of the drug vial 25 have emptied into the flexible bag 23, the flexible bag 23 may be raised above the fluid level in the IV bag 10. At this time, the clamp 22 in the second line 20 is opened so that the drug may be dispensed into the primary line 12 via the arm 21 of the Y-Site 18. After the desired amount of drug has been dispensed, the clamp 22 is again clamped into place to cut off any further flow from the second line 20 into the primary line 12.

Normally, the entire content of the drug within the flexible bag 23 is dispensed. When the height of the fluid in the second line 20 (normally in the tubing) is the same as the primary line 12 fluid height, then flow is initiated in the primary line. The remaining drug in the second line 20 is a very small quantity and is not dispensed.

Figure 10:
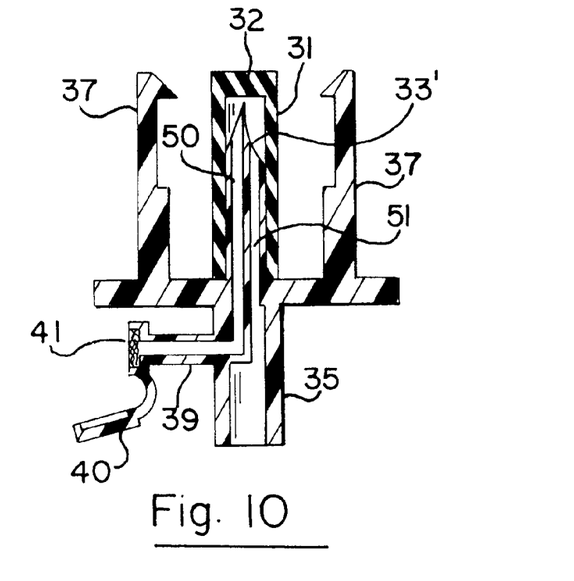
FIG. 10 illustrates a penetrating member having two lumen in accordance with the invention.

Referring to FIG. 10, wherein like reference characters indicate like parts as above, the hollow penetrating member 33' may be of double lumen type. As indicated, one lumen 50 of the member communicates directly with the air vent 39 to permit the venting of air from the spigot 35 which is connected to the second line 20 or flexible reservoir bag 23 (see FIG. 1). The second lumen 51 is connected directly with the spigot 35 so as to conduct fluid from a drug reservoir directly into and through the spigot 35.

Figure 11:
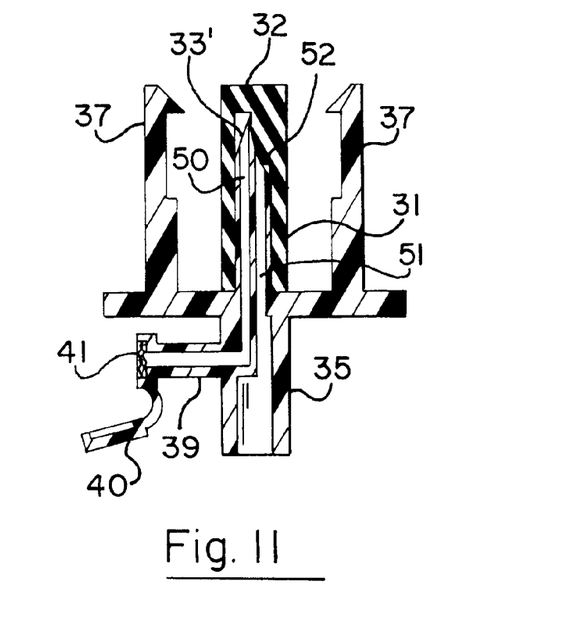
FIG. 11 illustrates a modified penetrating member in accordance with the invention.

Referring to FIG. 11 wherein like reference characters indicate like parts as above, the collapsible sleeve 31 may be provided with an enlarged shoulder 52 to seal the two lumen 50, 51 from each other prior to passage of the penetrating member 33' through the membrane 32. This will seal off the air vent 39 from the adaptor connection to the flexible bag (not shown) and tubing (not shown) to the primary line. In this way, the filter 41 may always be opened since only when the sleeve 31 is collapsed by the action of the bung of the vial (not shown) will the air vent line be in communication with the drug vial and, thence, with the flexible bag and the IV line. Thus, there is no need to open and close the air vent filter.

As illustrated, the shoulder 52 is formed by an upper portion of the collapsible sleeve 31 so as to fit about the extended portion of the penetrating member 33' while sealing off the opening of the second lumen 51.

Figure 12:
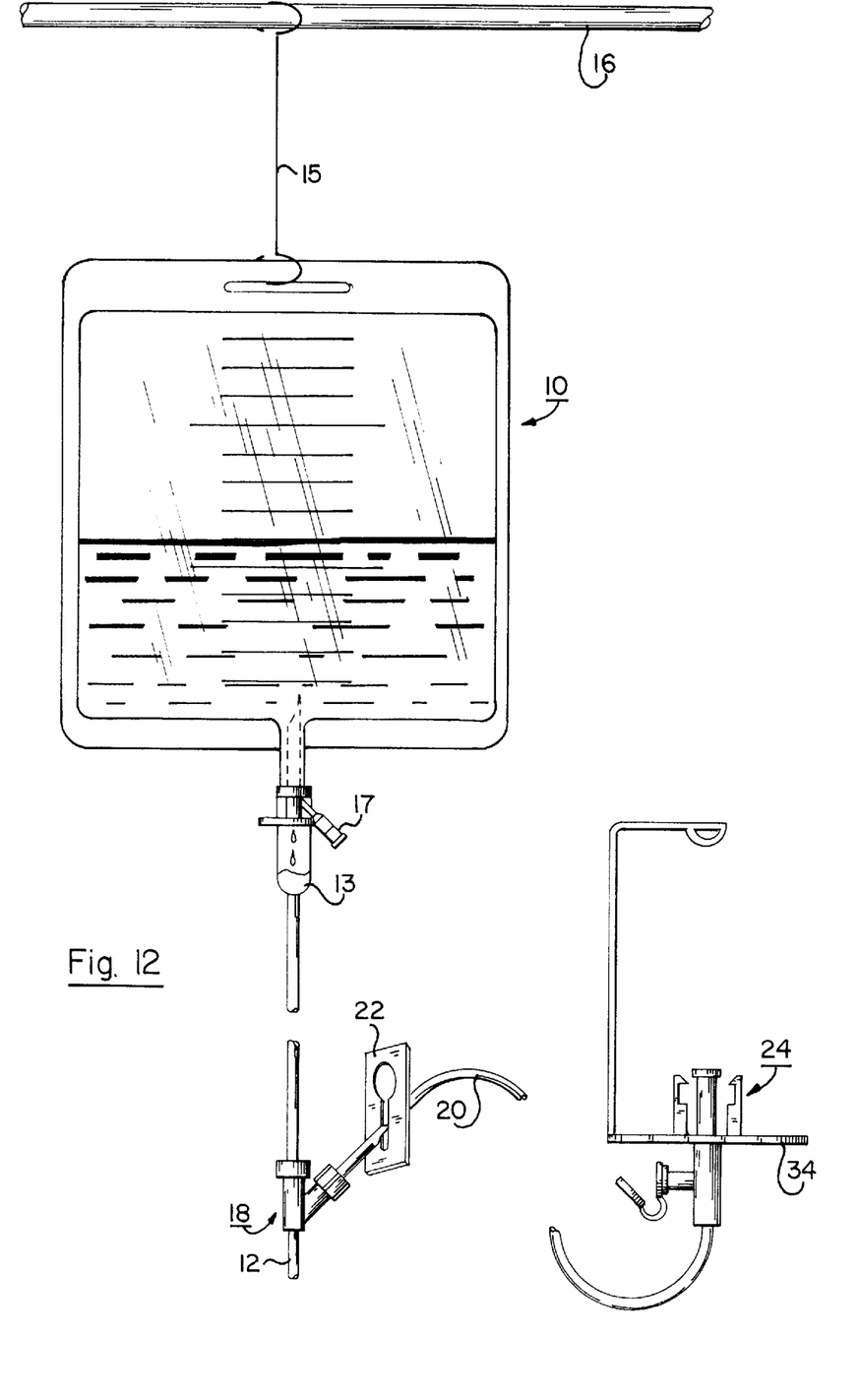
FIG. 12 illustrates a modified medication administering system in accordance with the invention with an air vent on the adaptor.

Referring to FIG. 12 wherein like reference characters indicate like parts as above, the medication administering system may be used without a fluid reservoir or bag 23 shown in the embodiment of FIG. 1. In this embodiment, the drug in a drug vial may be diluted by fluid in the second line 20 and subsequently dispensed directly into the second line 20. By way of example, once a drug vial has been coupled to the adaptor 24, the unit comprising the adaptor and the drug vial is inverted from the position shown in FIG. 12 so that fluid from the second line 20 may pass into the drug vial for reconstitution or diluting purposes. Thereafter, the unit consisting of the adaptor 24 in the drug vial is again placed in the position indicated in FIG. 12 so that the reconstituted or diluted drug may dispense directly from the drug vial into the second line 20. In this respect, the drug vial is first elevated above the level of the priming fluid prior to opening the clamp 22 and allowing drug to gravity feed into the primary line 12.

Figure 13:
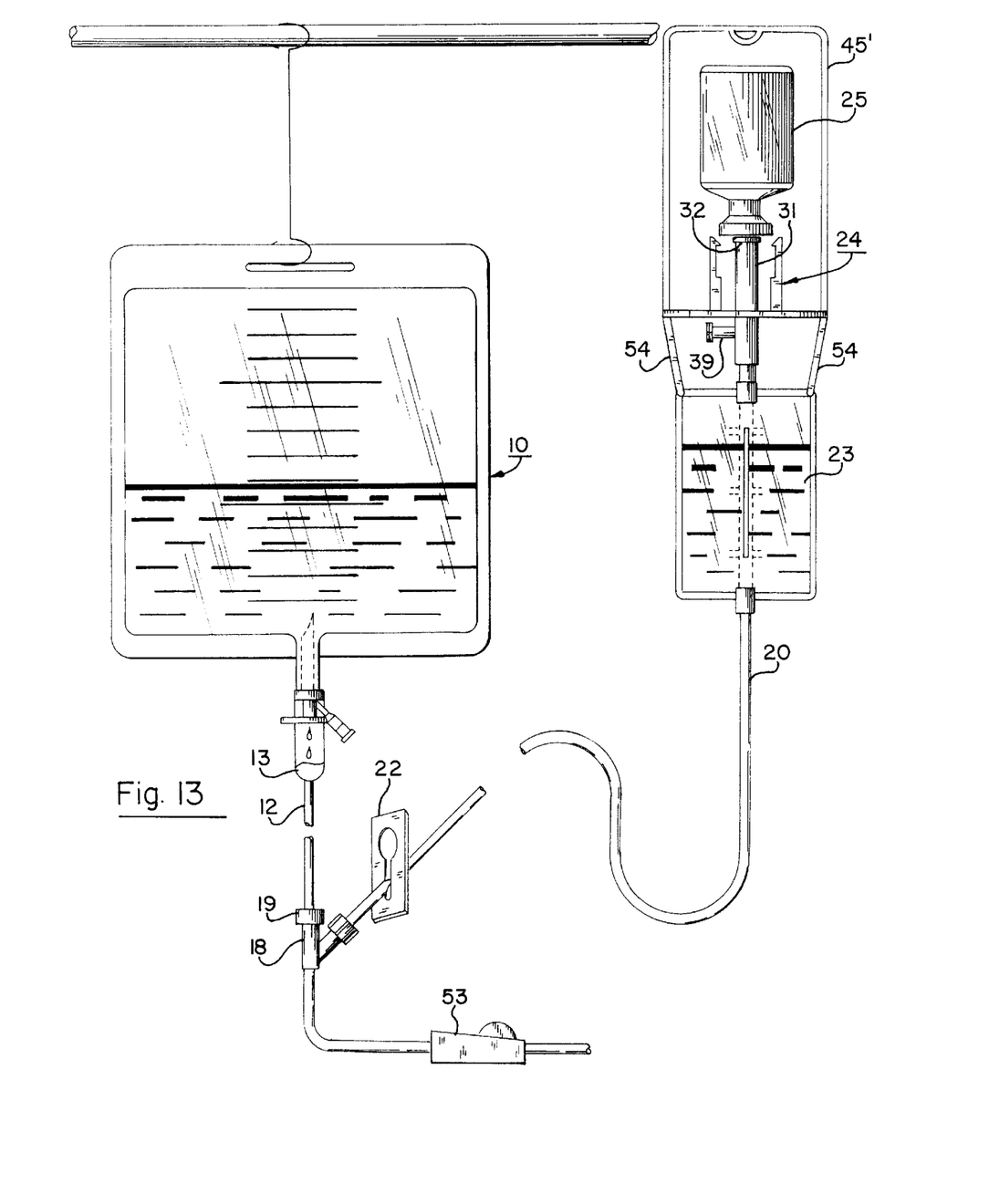
FIG. 13 illustrates a further modified medication administering system employing a modified hanger for mounting a drug vial.

Referring to FIG. 13, a flow control clamp 53, flow controller or IV pump may be provided in the primary line 12 upstream of the access device to control flow therethrough. Other modifications may also be made in the system. For example, the flexible reservoir bag 23 may be secured by a pair of articulated struts 54 to the base plate 34 of the adaptor 24. In addition, the hanger 45' may be of the closed loop type. A back check valve 19 may be placed with a slide clamp (not shown) or other suitable flow on/off device in line 12.

Figure 14:
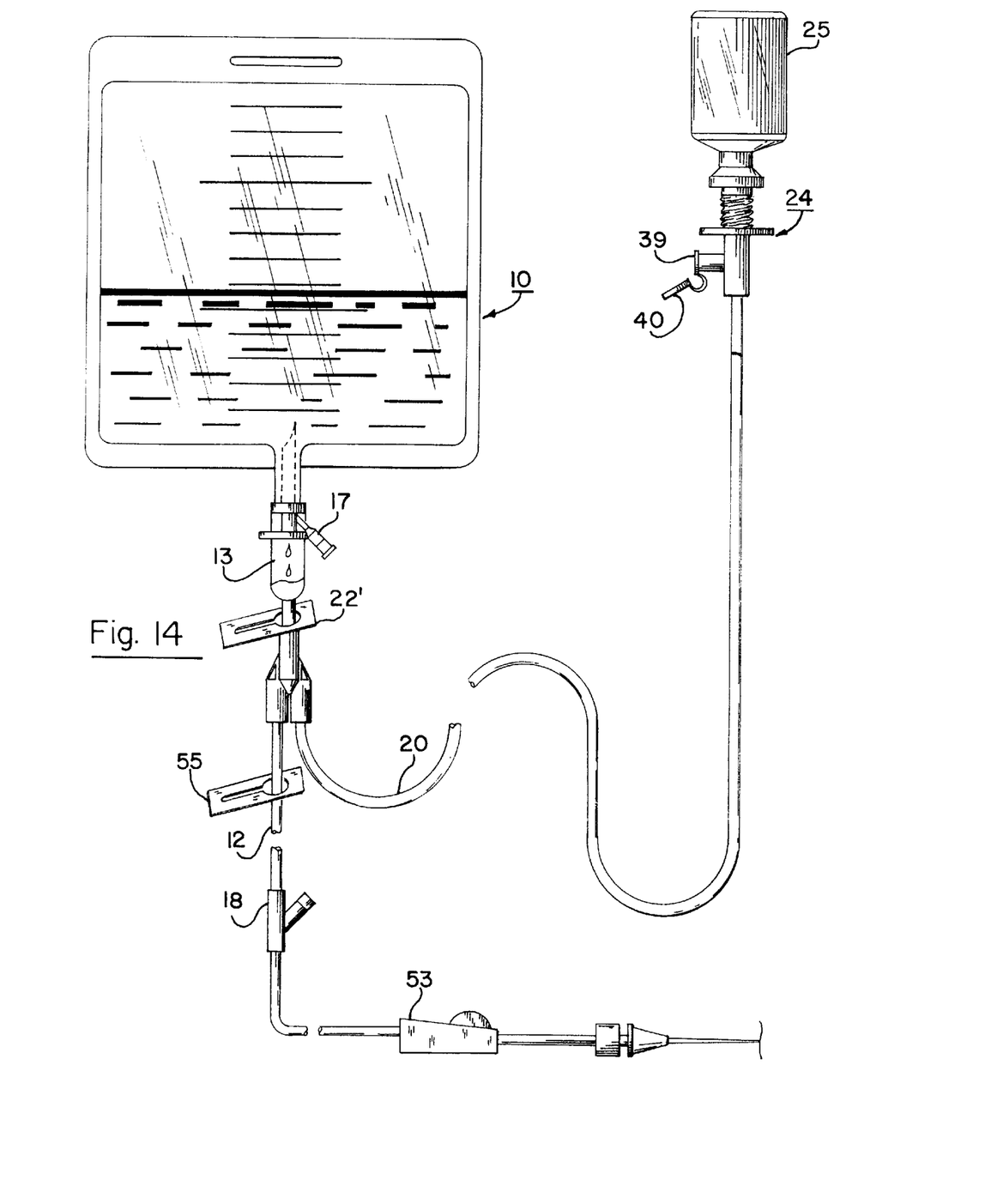
FIG. 14 illustrates a modified medication administering system having a primary line and second line connected in parallel to a drip chamber leading from an IV bag in accordance with the invention.

Referring to FIG. 14 wherein like reference characters indicate like parts as above, the second line 20 may be connected in parallel with the primary line 12 to the drip chamber 13. In this embodiment, a clamp 55 is provided on one or both of the lines 12, 20 so as to permit priming of the second line 20. In addition, a clamp 22' is also disposed in the primary line 12 below the drip chamber 13 in order to prevent back flow into the bag 10 should the vial be raised above the level of the bag 10.

Figure 15:
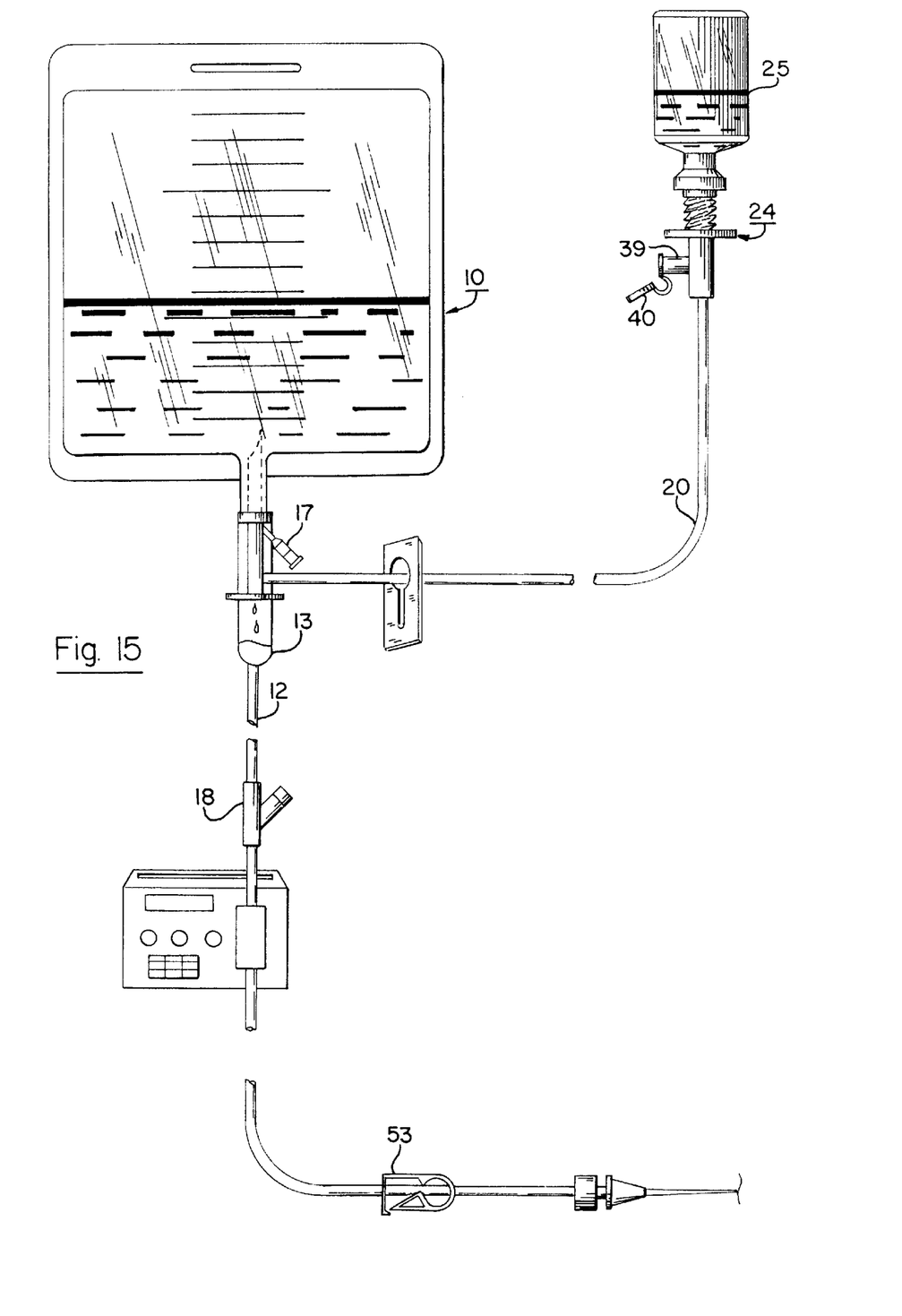
FIG. 15 illustrates a view similar to FIG. 14 of a further modified medication administering system having a second line connected between an IV bag and drip chamber in accordance with the invention.

Referring it FIG. 15 wherein like reference characters indicate like parts as above, the second line 20 may be connected upstream of the drip chamber 13, that is to a position between the IV bag 10 and the drip chamber 13. Flow control may be achieved by the use of a flow controller IV pump, flow control clamp or other similar device none of which are shown.

Figure 16:
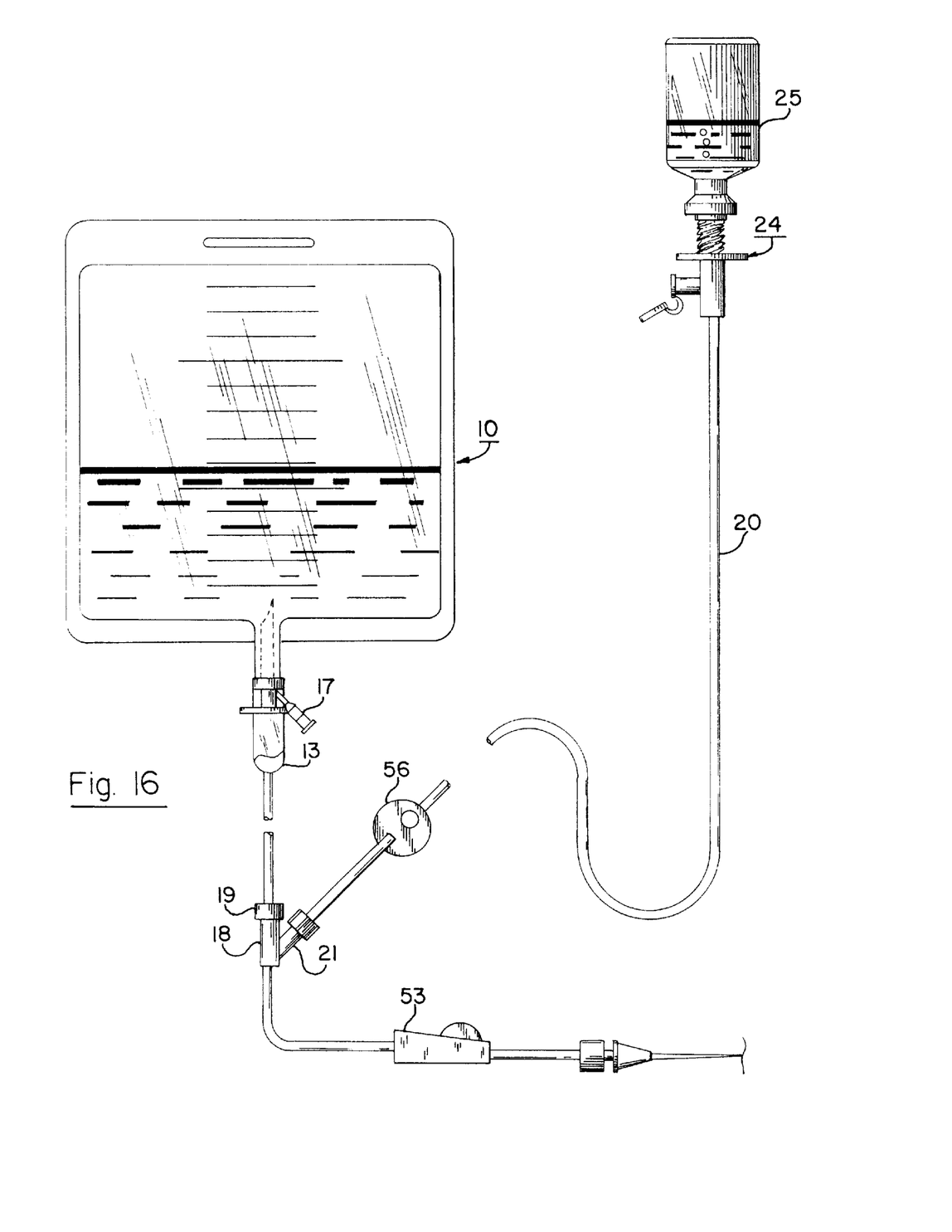
FIG. 16 illustrates a further modified medication administering system employing an air venting filter in the second line.

Referring to FIG. 16, the second line 20 may be provided with an air venting filter 56. Such a filter 56 will aide in preventing particles of unreconstituted drug from entering a patient's bloodstream.

Figure 17:
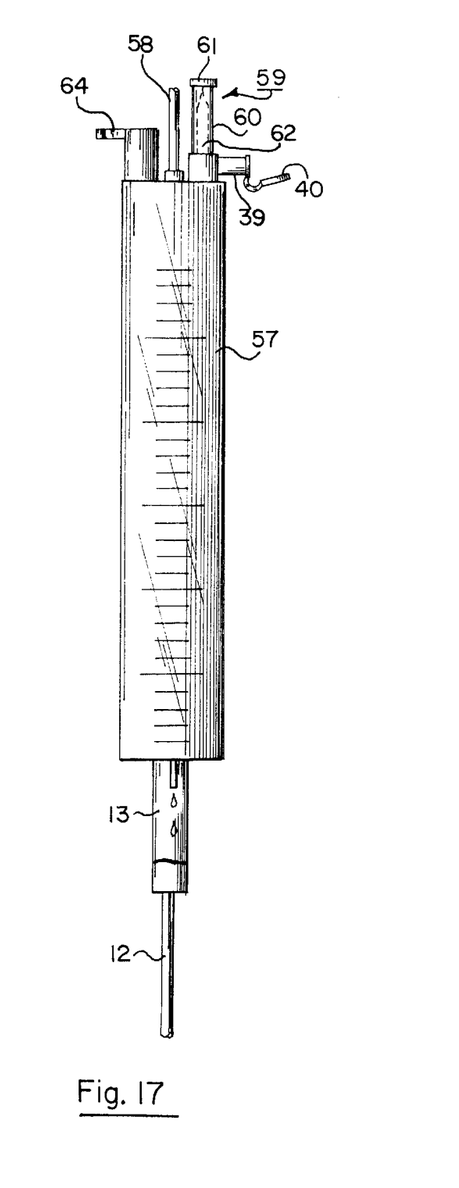
FIG. 17 illustrates a modified medication administering system employing a Buretrol tube for the mixing of a drug with a fluid.

Referring to FIG. 17, a squeezable volumetric control tube set such as a Buretrol® tube 57 may be connected via a primary line 58 to an IV bag (not shown) with a drip chamber 13 extending from the lower end of the tube 57 to communicate with the primary line 12. In this embodiment, an adaptor 59 is mounted on the upper end of the tube 57 for coupling with a drug delivery means such as a drug vial. As above, the adaptor 59 includes a collapsible sleeve 60 with a membrane 61 and a spike piercing cannula 62 disposed concentrically within the sleeve 60. An air vent 39 with a cap 40 is also provided to vent air from the spike 62. In addition, an air vent or valve 64 is also provided on the end of the tube 57 for venting air therefrom and has a cap to effect an on or off position.

In an alternative embodiment, the air vent 39 and cap 40 may be eliminated in order to permit the tube 57 to act as a charge drip chamber.

In use, the fluid from the IV bag fills the tube 57 to a desired amount. Thereafter, a drug vial can be coupled to the adaptor 59 in a manner as described above. Once a connection has been made, the tube 57 may be squeezed so as to allow fluid to pass from the reservoir of fluid in the tube 57 into the drug vial to reconstitute the drug therein. Returning the tube 57 to the position shown in FIG. 17 allows the reconstituted drug to pass into the tube 57 for subsequent dripping into the drip chamber 13 and subsequent passage into the primary line 12 to the patient. A filled drug vial when attached to the control tube 57 and when the air valve 64 is opened will empty directly into the tube 57.

Figure 18:
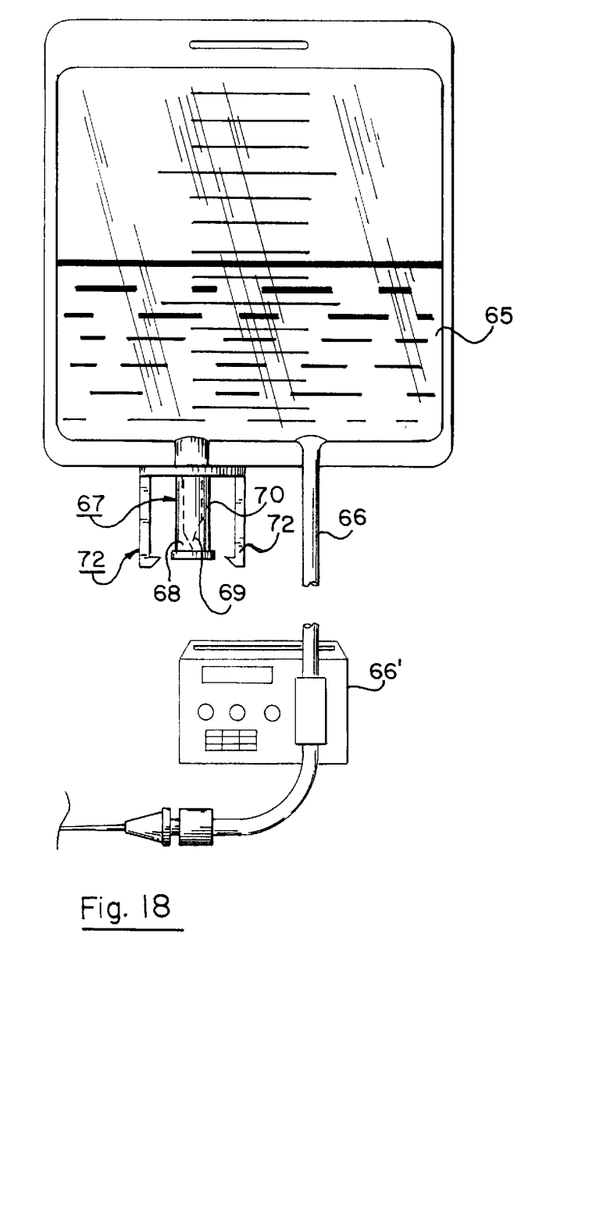
FIG. 18 illustrates a flexible bag employing an adaptor for coupling to a drug vial in accordance with the invention.

Referring to FIG. 18, a semi-rigid 65 may be provided with a line 66 which extends from the bag 65 to terminate at an injection site of a catheter attached to a patient. A flow control device 66' may form part of the line 66 to control the flow therethrough. In addition, an adaptor 67 extends from the bag 65 for coupling with a drug vial in a manner as described above. That is, the adaptor 67 includes a collapsible sleeve 68, a membrane 69 to close off one end of the sleeve and a hollow penetrating member 70 for piercing through the membrane 69 into a drug vial. An air vent (not shown) may also be provided for venting purposes when insufficient air is present in the bag along with a resilient locking means 72 in the form of a pair oppositely disposed prongs. In this embodiment, the penetrating member 70 is in direct communication with the interior of the bag 65. The drug vial (not shown) may be first filled then emptied or attached, pre-filled and emptied into the bag. In either case, the adaptor 67 with the filled vial would be elevated above the fluid level in the bag 65 to empty. In this embodiment, the line 66 is first primed and connected to the injection site before emptying the contents of the drug vial into the flexible bag 65.

In use, the bag 65 may be supplied pre-filled (normally half full) with fluid. After the drug vial has been connected, fluid within the bag 65 is allowed to pass into the drug vial to dilute to drug therein. The bag 65 is then inverted so that the contents of the drug vial can then be dispensed directly into the bag 65.

Thereafter, the bag 65 is again inverted into the position shown in FIG. 18 so that the diluted drug can pass through the line 66 to a patient.

Figure 19:
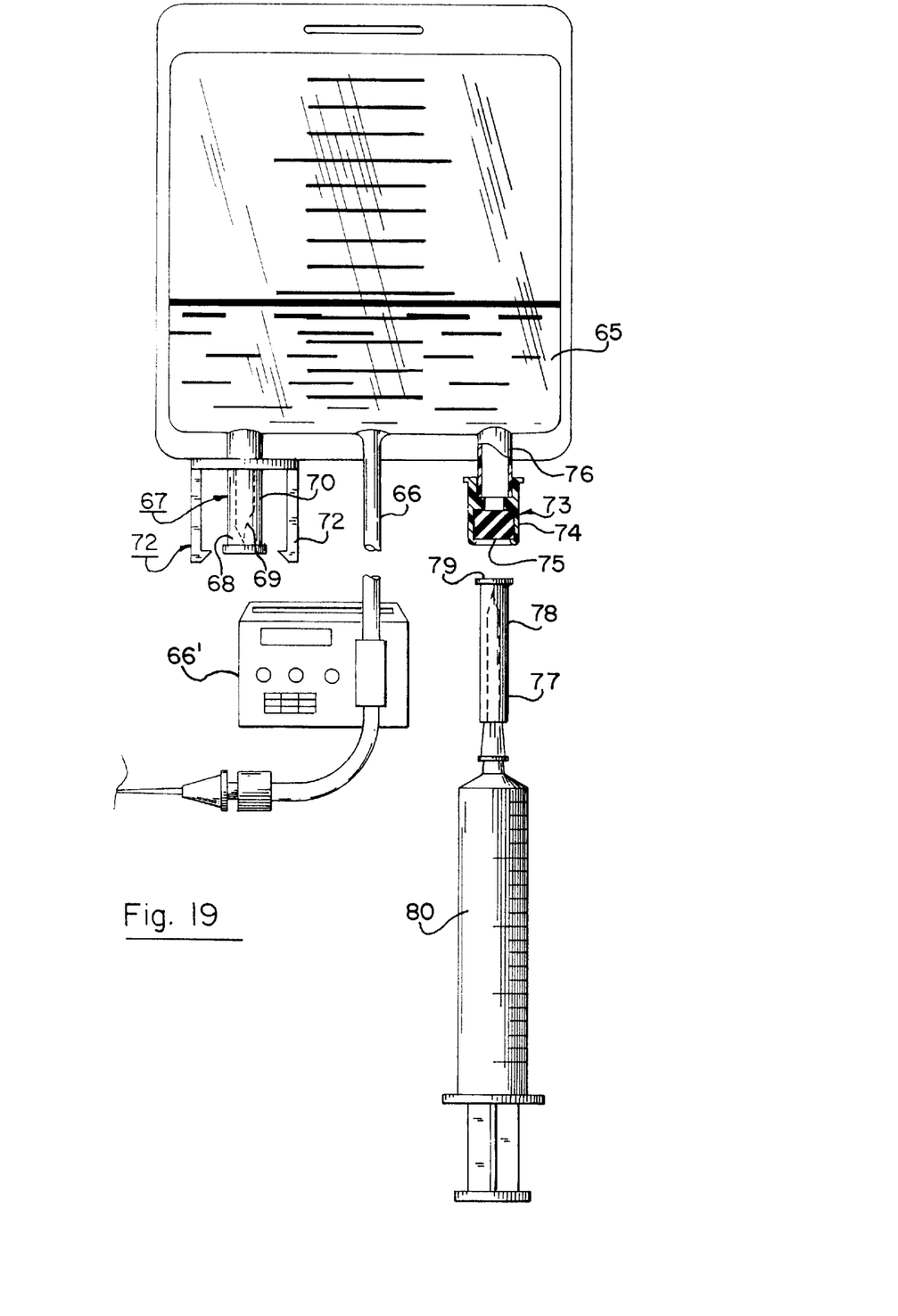
FIG. 19 illustrates a flexible bag similar to FIG. 15 having an injection site to be accessed by a syringe in accordance with the invention.

Referring to FIG. 19 wherein like reference characters indicate like parts as above, the flexible bag 65 may be further provided with an injection site 73 which is formed of a molded housing 74 into which is placed a rubber disc 75. This disc 75 is secured to the housing 74 so as to be locked in place in order to prevent leakage of fluid from the interior of the housing 74 (fluid path) to the outside. This rubber disc 75 may be unitary (solid) to accommodate needles or pre-slit to accept blunt-type cannula for penetrating purposes. As illustrated, the molded housing 74 fits over a port 76 or the like extending from flexible bag 65. Any suitable type of sealing arrangement may be made between the housing 74 and the port 76 to ensure a seal-tight fit.

As indicated, a penetrating member 77, as above, is disposed within a collapsible sleeve 78 having a septum 79 at one end which may be pre-slit to accommodate a blunt cannula. For a sharp cannula, no pre-slit is required. The proximal end of the sleeve 77 is connected to a reservoir, such as a syringe 80 containing sterile fluid.

A sterile connection may be made between the syringe 80 and the injection site 75 in a manner as above. For example, the rubber disc 75 and the septum 79 may be wiped with a suitable disinfectant and then the septum 79 of the sleeve 78 may be pressed against the rubber disc 75 via the syringe 80. Upon further movement of the syringe 80 towards the injection site 73, the penetrating member 77 penetrates through the septum 79 and the rubber disc 75 into the port 76 to effect a fluid communication between the hollow penetrating member 77 and the interior of the bag 65.

The invention thus provides a relatively simple technique for connecting a drug vial in a sterile procedure to an IV administration set. Further, the invention provides a closed system medication administering system which can be easily manipulated by a nurse or other technician and which does not require any special infrared generating devices or devices for placing a charge molten plastic material about a connection.

What is claimed is:

1. A closed system medication administering system comprising
    an IV container for dispensing a fluid under gravity;
    a primary line communicating with said IV container to receive and convey fluid therefrom;
    an access device communicating with said primary line to deliver fluid to a patient;
    a Y-site connector in said primary line having a side arm communicating with said primary line;
    an adaptor for coupling with a drug vial, said adaptor including a collapsible sleeve with a membrane disposed across one end to seal against a hollow penetrating member contained within said sleeve for penetrating through said membrane into said vial in response to said sleeve collapsing; and
    a second line communicating with said penetrating member to receive the contents of the drug vial and communicating with said arm of said Y-site to deliver the vial contents to said primary line.

2. A system as set forth in claim 1 wherein said adaptor includes a resilient locking means for releaseably engaging with a drug vial.

3. A system as set forth in claim 2 wherein said locking means includes a pair of oppositely facing prongs, each said prong having at least one inwardly directed projection for engaging with a recessed portion of a drug vial.

4. A system as set forth in claim 1 which further comprises a hanger having said adaptor mounted thereon for suspending said adaptor from a support.

5. A system as set forth in claim 1 wherein said adaptor includes an air vent for venting air therefrom and a cap for selectively sealing said air vent.

6. A system as set forth in claim 5 wherein said air vent communicates with the interior of said hollow penetrating member.

7. A system as set forth in claim 5 wherein said hollow penetrating member has a pair of parallel lumen, one of said lumen communicating with said air vent and the other of said lumen communicating with said second line.

8. A system as set forth in claim 1 which further comprises a releasable clamp on said second line for selectively blocking flow through said second line.

9. A system as set forth in claim 1 further comprising a flexible bag disposed between and in communication with said penetrating member and said second line to receive fluid from one of said penetrating member and said second line.

10. A system as set forth in claim 9 which further comprises a support secured to one exterior side of said bag and a pull tab secured to an opposite exterior side of said bag for selectively pulling said sides apart to draw a vacuum in said spike for emptying the contents of a drug vial.

11. A system as set forth in claim 1 further comprising an air venting filter in said secondary line.

12. A closed system medication administering system comprising
    an IV container for dispensing a fluid under gravity;
    a drip chamber in communication with said IV container;
    a primary line communicating with said drip chamber to receive and convey fluid therefrom;
    an access device communicating with said primary line to deliver fluid to a patient;
    an adaptor for coupling with a drug vial, said adaptor including a collapsible sleeve with a membrane disposed across one end to seal against a hollow penetrating member contained within said sleeve for penetrating through said membrane into said vial in response to said sleeve collapsing;
    a second line connected to said drip chamber in parallel with said primary line, said second line communicating with said penetrating member to receive the contents of the drug vial and communicating with said primary line to deliver the vial contents thereto; and
    a clamp for selectively closing at least one of said primary line and said second line.

13. A system as set forth in claim 12 wherein said adaptor includes an air vent for venting air therefrom and a cap for selectively sealing said air vent.

14. A closed system medication administering system comprising
    an IV container for dispensing a fluid under gravity;
    a drip chamber in communication with said IV container;
    a primary line communicating with said drip chamber to receive and convey fluid therefrom;
    an access device communicating with said primary line to deliver fluid to a patient;
    an adaptor for coupling with a drug vial, said adaptor including a collapsible sleeve with a membrane disposed across one end to seal against a hollow penetrating member disposed concentrically within said sleeve for piercing through said membrane into said vial in response to said sleeve collapsing;
    a second line communicating with said penetrating member to receive the contents of the drug vial and connected between said IV container and said drip chamber to deliver the vial contents to said drip chamber; and a flow control device for controlling flow through said second line.

15. A system as set forth in claim 14 wherein said adaptor includes an air vent for venting air therefrom and a cap for selectively sealing said air vent.

16. A system as set forth in claim 14 wherein said flow control device is a releasable clamp on said second line for selectively blocking flow through said second line.

17. A closed system medication administering system comprising an IV container for dispensing a fluid under gravity;

a volume control tube connected to said IV container to receive fluid therefrom;

a drip chamber extending from said tube;

a primary line extending from said drip chamber to convey fluid therethrough;

an adaptor on one end of said tube for coupling with a drug delivery means, said adaptor including a collapsible sleeve with a membrane disposed across one end to seal against the drug delivery means and a hollow penetrating member concentrically within said sleeve for penetrating through said membrane into the drug delivering means in response to said sleeve collapsing; and an air vent on said one end of said tube for venting air therefrom.

18. In combination, a bag for receiving fluid;

a line extending from said bag to convey fluid therebetween; and an adaptor extending from said bag for coupling with a drug vial, said adaptor including a collapsible sleeve with a membrane disposed across one end to seal against a hollow penetrating member within said sleeve for penetrating through said membrane into said vial in response to said sleeve collapsing; said penetrating member being in communication with said bag.

19. The combination as set forth in claim 18 wherein said adaptor includes a resilient locking means for releaseably engaging with a drug vial.

20. The combination as set forth in claim 19 wherein said locking means includes a pair of oppositely facing tangs, each said tang having at least one inwardly directed projection for engaging with a recessed portion of a drug vial.

21. The combination as set forth in claim 18 further comprising an injection site communicating with said bag, said site including a housing and a rubber disc within said housing to seal said site.

22. The combination as set forth in claim 21 further comprising a reservoir, a collapsible sleeve communicating with said reservoir, a membrane across one end of said sleeve and a hollow penetrating member within said sleeve and communicating with said reservoir for penetrating said rubber disc of said injection site.

23. The combination as set forth in claim 22 wherein said reservoir is a syringe.

24. A closed system medication administering system comprising an IV container for dispensing a fluid under gravity;

a drip chamber in communication with said IV container;

a primary line communicating with said drip chamber to receive and convey fluid therefrom;

an access device communicating with said primary line to deliver fluid to a patient;

an adaptor for coupling with a drug vial, said adaptor including a collapsible sleeve with a membrane disposed across one end to seal against a hollow penetrating member contained within said sleeve for penetrating through said membrane into said vial in response to said sleeve collapsing; and a second line communicating with said penetrating member to receive the contents of the drug vial and communicating with said primary line below said drip chamber to deliver the vial contents thereto.

25. A system as set forth in claim 24 wherein said adaptor includes an air vent for venting air therefrom and a cap for selectively sealing said air vent.

* * * * *